United States Patent
Blum et al.

(10) Patent No.: US 7,533,993 B2
(45) Date of Patent: May 19, 2009

(54) METHOD AND APPARATUS FOR CORRECTING VISION USING AN ELECTRO-ACTIVE PHOROPTER

(75) Inventors: Ronald D. Blum, Roanoke, VA (US); William Kokonaski, Gig Harbor, WA (US); Dwight P. Duston, Laguna Niguel, CA (US)

(73) Assignee: E-Vision, LLC, Roanoke, VA (US)

( * ) Notice: Subject to any disclaimer, the term of this patent is extended or adjusted under 35 U.S.C. 154(b) by 1 day.

(21) Appl. No.: 11/968,102

(22) Filed: Dec. 31, 2007

(65) Prior Publication Data

US 2008/0246922 A1    Oct. 9, 2008

Related U.S. Application Data

(63) Continuation of application No. 11/812,194, filed on Jun. 15, 2007, which is a continuation of application No. 10/772,917, filed on Feb. 5, 2004, now Pat. No. 7,264,354, application No. 11/968,102, which is a continuation-in-part of application No. 10/626,973, filed on Jul. 25, 2003, now Pat. No. 6,918,670, which is a continuation of application No. 09/602,013, filed on Jun. 23, 2000, now Pat. No. 6,619,799.

(60) Provisional application No. 60/446,173, filed on Feb. 6, 2003, provisional application No. 60/161,363, filed on Oct. 26, 1999, provisional application No. 60/150,564, filed on Aug. 25, 1999, provisional application No. 60/150,545, filed on Aug. 25, 1999, provisional application No. 60/147,813, filed on Aug. 10, 1999, provisional application No. 60/143,626, filed on Jul. 14, 1999, provisional application No. 60/142,053, filed on Jul. 2, 1999.

(51) Int. Cl.
    *A61B 3/02* (2006.01)

(52) U.S. Cl. ........................ 351/233; 351/228

(58) Field of Classification Search ................. 351/222, 351/227–231, 233–236
    See application file for complete search history.

(56) References Cited

U.S. PATENT DOCUMENTS

| 3,791,719 | A |   | 2/1974  | Kratzer et al. |
|-----------|---|---|---------|----------------|
| 4,601,545 | A | * | 7/1986  | Kern ........................... 349/200 |
| 5,815,233 | A | * | 9/1998  | Morokawa et al. .......... 349/200 |
| 2002/0140899 | A1 | | 10/2002 | Blum et al. |
| 2002/0186346 | A1 | | 12/2002 | Stantz et al. |

FOREIGN PATENT DOCUMENTS

EP      04708610.3      11/2005

OTHER PUBLICATIONS

India Office Action of Application No. 03192/DELNP/2005, dated Sep. 4, 2008.
Australia Offic Action of Application No. 2004211216, dated Jul. 23, 2008.

* cited by examiner

*Primary Examiner*—Huy K Mai
(74) *Attorney, Agent, or Firm*—Pearl Cohen Zedek Latzer, LLP

(57) ABSTRACT

An electro-active phoropter and a method of using the electro-active phoropter to measure a patient's vision prescription is disclosed. The electro-active phoropter includes a series of individually addressable electro-active lenses. The lenses have either a positive or negative optical power when an electrical potential is applied across the lens and a neutral optical power when no electrical potential is applied across the lens. Each lens provides an optical power that is part of a net optical power of the series of lenses when a patient views through the phoropter. The optical power of the phoropter can be incrementally adjusted by changing the distribution of the electrical potential across the different lenses of the series to provide increasing or decreasing optical power until a patient achieves a desired level of clarity and a vision prescription has been determined.

11 Claims, 10 Drawing Sheets

Spatial Voltage Profile for a Diverging Electro-active Lens

Spatial Voltage Profile for a Converging Electro-active Lens

METHOD AND APPARATUS FOR CORRECTING VISION USING AN ELECTRO-ACTIVE PHOROPTER

RELATED APPLICATIONS

This application is a continuation of U.S. patent application Ser. No. 11/812,194 filed on Jun. 15, 2007, which is a continuation of U.S. patent application Ser. No. 10/772,917, now U.S. Pat. No. 7,264,354, filed on Feb. 5, 2004, which in turn claims priority to U.S. Provisional Patent Application No. 60/446,173 filed on Feb. 6, 2003. The application is also a continuation in part of U.S. patent application Ser. No. 10/626,973, filed on Jul. 25, 2003 now U.S. Pat. No. 6,918,670, which is a continuation of U.S. patent application Ser. No. 09/602,013, now U.S. Patent No. 6,619,799, filed on Jun. 23, 2000, which claims priority to U.S. Provisional Patent Application Nos. 60/142,053 filed on Jul. 2, 1999; 60/143,626 filed on Jul. 14, 1999; 60/147,813 filed on Aug. 10, 1999; 60/150,545 filed on Aug. 25, 1999; 60/150,564 filed on Aug. 25, 1999; and 60/161,363 filed on Oct. 26, 1999.

FIELD OF THE INVENTION

The present invention relates to the field of vision correction, and, more particularly, to an apparatus and method for correcting vision using an electro-active phoropter.

SUMMARY OF THE INVENTION

A system and method for determining a vision prescription using an electro-active phoropter is disclosed. The inventive electro-active phoropter for determining a vision prescription comprises individually addressable electro-active lenses in series and a power source connected to each of the electro-active lenses to apply an electric potential across each electro-active lens and create a positive, negative, of neutral optical power in each electro-active lens.

A method for determining a vision prescription using an electro-active phoropter is also disclosed. The method uses an electro-active phoropter comprising individually addressable electro-active lenses in series and a power source connected to each of the electro-active lenses to individually create one of a positive, negative, or neutral optical power in each electro-active lens. The method comprises providing electrical power to at least one electro-active lens to produce a net optical power in the series of electro-active lenses other than 0 diopters, individually varying the electrical power to each of the electro-active lenses to create an incremental change of net optical power to a patient's eyes until a desired level of vision correction is achieved, and recording the vision prescription that corresponds to the net optical power of the series of lenses at the desired level of vision correction. It should be appreciated, that in some cases, the appropriate optical power could be zero diopters.

Aspects of the present invention will now be described in more detail with reference to exemplary embodiments thereof as shown in the appended drawings.

DETAILED DESCRIPTION OF EXEMPLARY EMBODIMENTS

Figure 1:
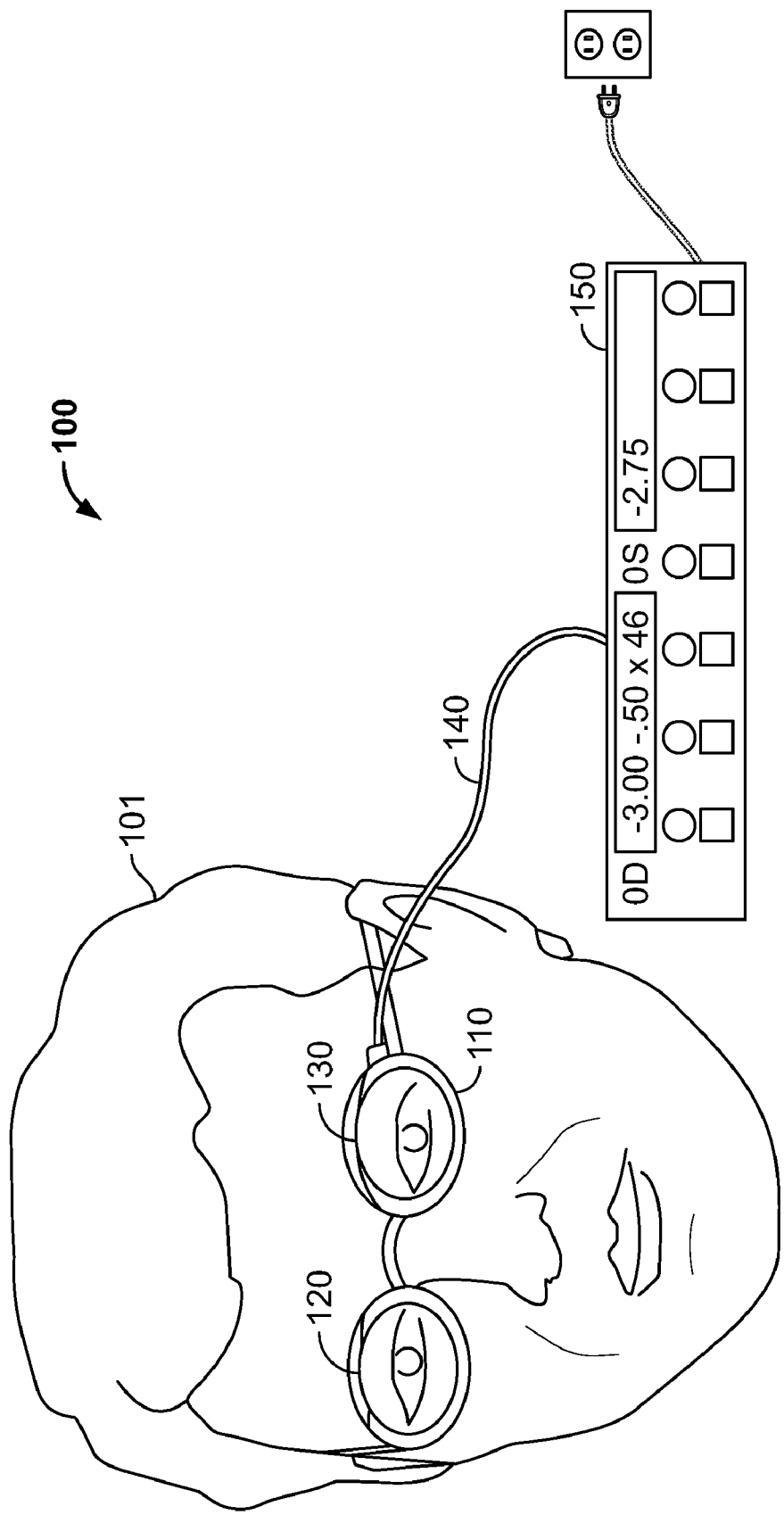
FIG. 1 illustrates electro-active eyeglasses in accordance with an exemplary embodiment of the invention.

Conventional devices for determining vision prescriptions typically involve a mechanical phoropter that uses lenses of different spherical and cylindrical powers that are mechanically or electro-mechanically moved in front of a patient's eye by an optometrist or other eye care professional. The various lenses of the phoropter may be flipped or rotated in front of the patient's eye while the patient looks through the lenses at an eye chart. A vision prescription may then be determined for the patient based on the optical power of the lenses that give the patient satisfactory and appropriate vision correction for each eye.

Exemplary embodiments of the present invention are directed to an electo-active phoropter and its use for determining a patient's vision prescription. By "phoropter" is meant any ophthalmic instrument for measuring and correcting an individual's vision, including devices known as refractors, for example. The phoropter comprises electro-active lenses in series. Each electro-active lens is individually addressable so that each electro-active lens may have an optical power independent of the other lenses in the series. The optical power of each lens may be a positive, negative or no (neutral) optical power. The optical power is individually varied in each electro-active lens by an electrical potential created across that particular electro-active lens. The phoropter also comprises a power source that is connected to electro-active lenses to create the electrical potential across the various electro-active lenses.

The electro-active lenses contain an electro-active material that can be used to vary the optical power of the lens. Electro-active material includes materials with a modifiable index of refraction, such as nematic liquid crystals for example, that orient in a particular manner when an electrical potential is applied to them. When an electrical potential is applied across the area of a lens that contains the electro-active material, the change in orientation creates a change in the material's index of refraction and correspondingly, creates a change in the optical power of the lens.

Each electro-active lens is individually addressable so that one electrical potential can be applied across one electro-active lens while a different, or no, electrical potential is applied across one or more other electro-active lenses in the series. The optical power of each lens is additive and a series of lenses, each having a different optical power, creates a net optical power that is the sum of the optical power of each of the individual lenses.

In some embodiments of the invention, the electro-active lens may be finely pixelated. In these embodiments, the electro-active material is separated into a grid to create a plurality of fine pixels. The grid of fine pixels may cover any area of the lens, such that the lens is fully, mostly, or partially pixelated.

Each fine pixel is connected to a separate electrode and is individually addressable so that not only can a different electrical potential be applied to a different lens in the series, but a different electrical potential can be applied to different areas of the same lens by activating certain fine pixels and not others. This is particularly advantageous for measuring and correcting non-conventional refractive error- or, higher order aberrations such as coma, spherical aberrations, and the like.

It should be appreciated that in one preferred embodiment, a finely pixelated electro-active lens is utilized in combination with individually addressable fixed pattern pixelated electro-active lenses. In this case, the individually addressable fixed pattern pixelated electro-active lenses measure and correct for the vast majority of optical powers needed and the finely pixelated electro-active lens measures and corrects for the higher order aberrations. In other embodiments, the finely pixelated electro-active lens is used in combination with a plurality of conventional lenses. In these embodiments, the conventional lenses measure and correct for conventional refractive error and the finely pixelated lens measures and corrects for higher order aberrations. It may also be used to fine tune either the spherical or astigmatic errors of the eye corrected by the conventional lenses.

The distance between the lenses in series is typically minimized, with a preference to stack the lenses in the series adjacent one another. Decreasing the distance between lenses reduces distortions when a patient looks through the series of lenses. Further, stacking the lenses adjacent one another may permit construction of thinner phoropters, which need only be as thick as the width of the lenses themselves. However, when stacking lenses, care must be taken to provide enough electrical insulation between lenses to prevent the electrical field of one electro-active lens from substantially affecting the electric field of adjacent electro-active lenses. To lessen this effect, the lenses may be separated by a ground plane layer.

The electro-active phoropter may comprise a single series of lenses that a patient can look through with either eye, typically one eye at a time, thus always determining the patient's monocular visual needs. However in the preferred embodiment, the phoropter is arranged in such a way as to determine one or both of the patient's monocular and binocular vision needs by measuring and correcting one or both of the patient's monocular and binocular refractive error Preferably, the phoropter comprises two separate series of lenses, one series for each eye, that are arranged in a side-by-side fashion so that both eyes can be examined individually or together without the need to move either the patient or the phoropter. An individual eye may be examined by blocking vision through the lens series of the eye not undergoing examination, such as by covering one end of the lens series with an opaque item like a patch or shield, for example. A phoropter that comprises two series of lenses also has the advantage of measuring and correcting the patient's vision correction in both eyes at the same, also known as binocular-vision. This may ensure that the vision correction measured for each eye is still a correct measurement when the patient is viewing with both eyes, which is usually the case in normal vision. It may also allow the patient to ascertain how a new vision prescription will appear.

The electro-active lenses of the phoropter may be attached to or contained within a frame or other type of support to form a single unit that can easily be moved into or out of the patient's line of sight. Because the need to mechanically rotate lenses into or out of the series of lenses is reduced or eliminated in certain embodiments of the invention, the series of lenses may be placed within a frame, such as an eyeglass frame for example that the patient can wear during the refraction procedure as shown in FIG. 1. A phoropter 100 comprises two series of lenses, 120, 130, each of which are created to fit within the phoropter frame 110. The phoropter frame 110 can easily be worn by a patient 101 while the lenses within each of the series are connected to a control unit 150 via a bundle of conductors 140 that acts as a power source and provides electrical power to each electron-active lens in the series of lenses 120, 130 to create the desired optical power for each eye.

Figure 2:
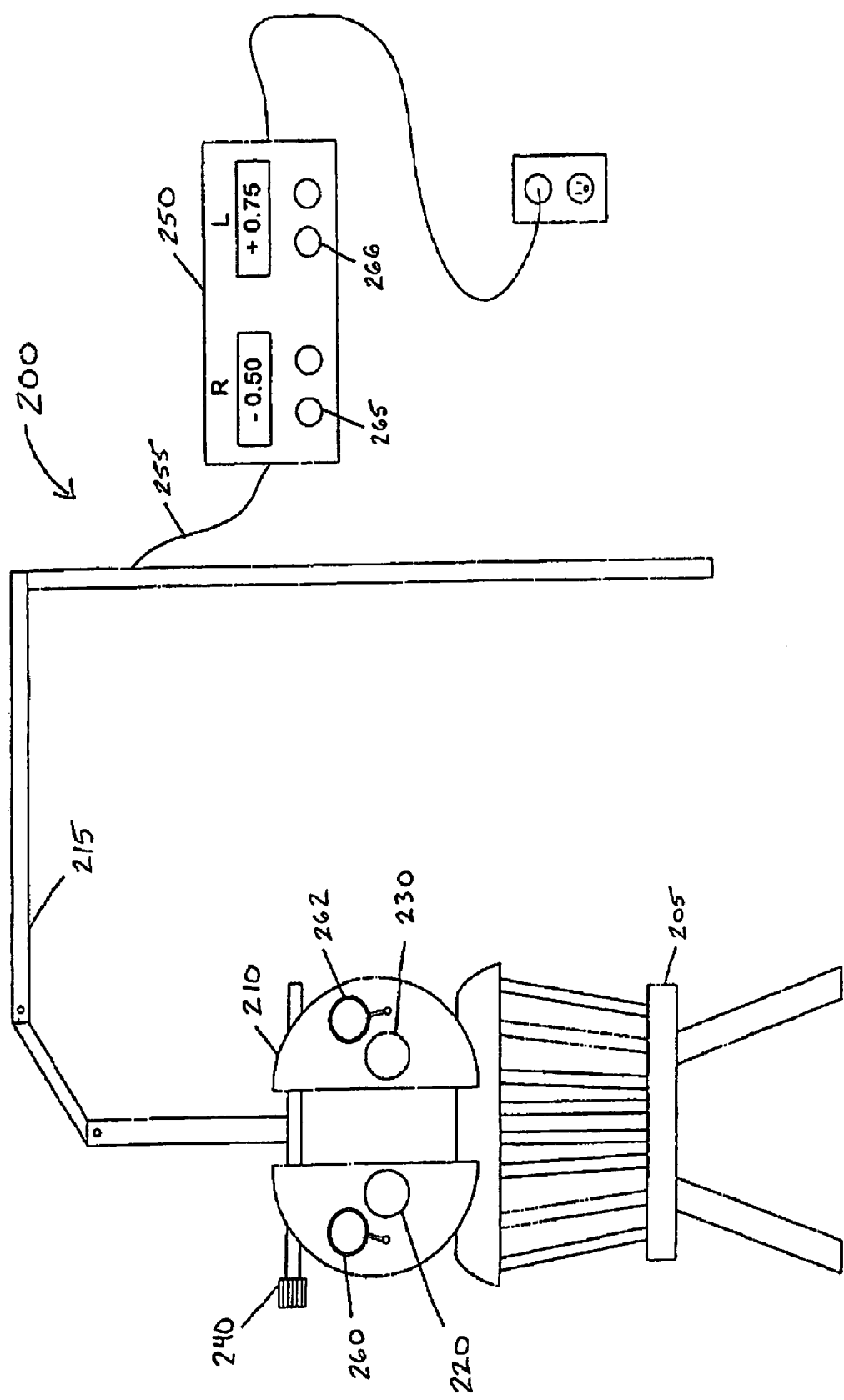
FIG. 2 illustrates an electro-active phoropter in accordance with another exemplary embodiment of the invention.

In another exemplary embodiment, the support may hold the series of lenses such that the phoropter support is viewed through, but not worn, by the patient, resembling a more conventional phoropter housing as shown in FIG. 2. A phoropter 200 comprises two series of lenses 220, 230 each of which are housed within the phoropter housing 210. The phoropter housing 210 may be connected to a hinged frame assembly 215 that allows an eye-care professional to raise or lower the phoropter housing 210 to place the series of lenses 220, 230 in front of a patient's eyes while the patient is sitting in a seat 205. An expansion rod 240 or other device may be used to increase or decrease the distance between the series of lenses 220, 230. This allows the phoropter housing 210 to be adjusted for use by patients having different facial characteristics, such as varying distances between the pupils, for example. The phoropter 200 also includes a control unit 250 that is an electrical power source connected to the series of lenses 220, 230 by a bundle of conductors 255 running through the hinged frame assembly 215 to each of the electro-active lenses within the phoropter housing 210.

The phoropter housing 210 may also include one or more conventional lenses 260, 262 that may be mechanically or electro-mechanically rotated into or out of the series of lenses, 220, 230 such as, by way of example only, to correct astigmatic error; to refine the prescription to within 125 diopters of accuracy, or to produce larger refractive power that may be impractical to produce with electro-active lenses.

Figure 3:
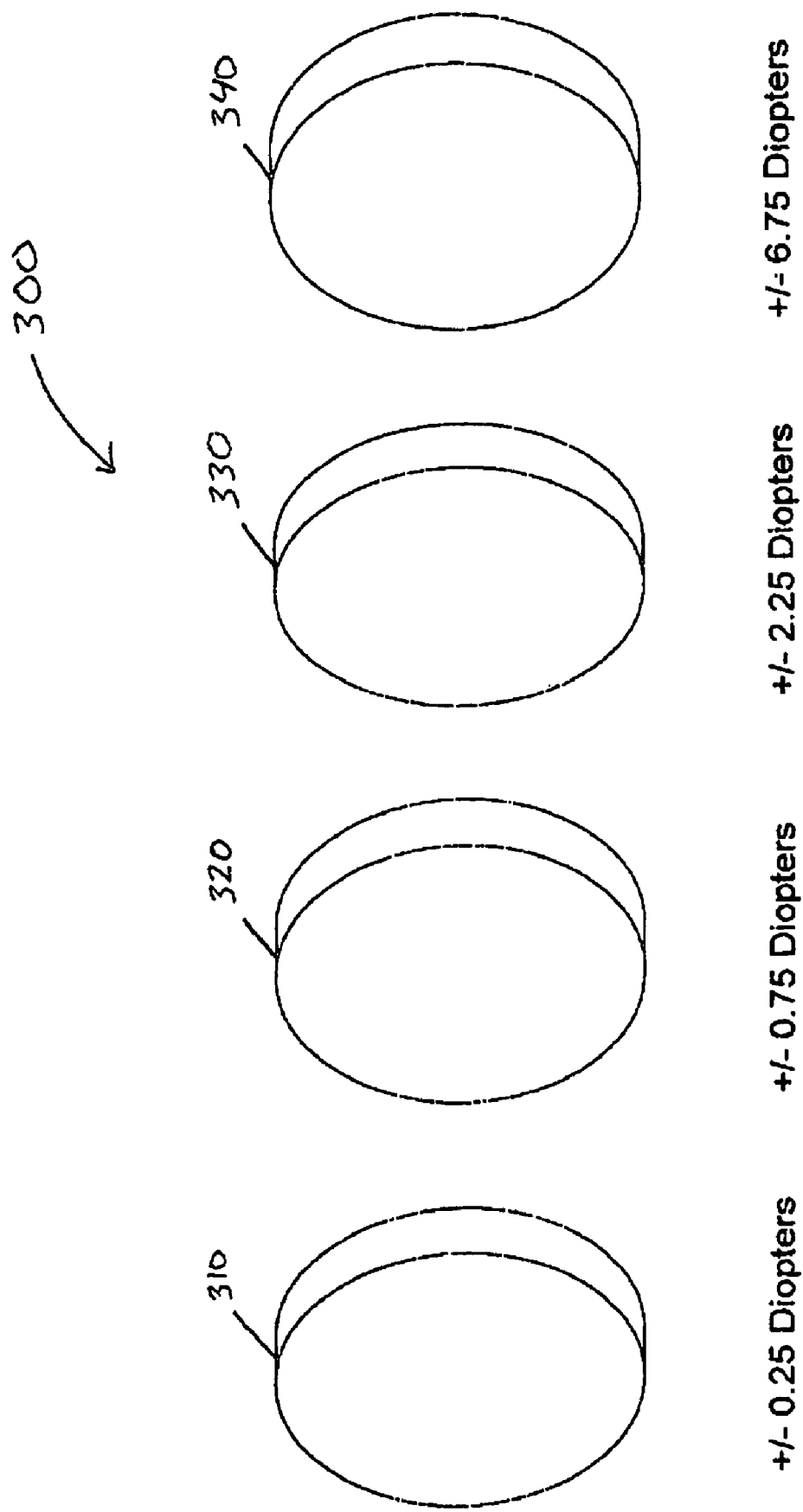
FIG. 3 illustrates a series of lenses of an electro-active phoropter in accordance with an exemplary embodiment of the invention.

In one exemplary embodiment of the invention as shown in FIG. 3, the electro-active phoropter comprises a series 300 of four lenses 310, 320, 330, 340. At least three of the lenses are electro-active. In this embodiment, the electro-active phoropter can produce a net spherical optical power ranging from −10.0 to +10.0 diopters (D) in steps of 0.25 D. This range of optical power corresponds to the range of nearly all patients who are in need of vision correction and who are capable of having their vision corrected using lenses. The increment of measurement, 0.25 D, represents the most common increment of measuring increasing of decreasing optical power.

It should be appreciated that while an optical power of −10.0 to +10.0 D is discussed, a wider or narrower range of optical powers is possible by adding or removing lenses from the phoropter or by increasing or decreasing the optical power of the lenses used. If additional lenses are desired they may be either conventional or electro-active.

A first electro-active lens 310 in this embodiment has an optical power of 0.25 D when the electro-active lens 310 is activated. By activated is meant that electrical power is supplied to the electro-active lens from the power source to create an electrical potential across the lens and cause the electro-active material of the lens to orient in a way that changes its index of refraction. The optical power in the activated electro-active lens is one of either a positive (converging) or negative (diverging) power; depending on the distribution of the electrical potential applied across the electro-active lens 310.

For example, a positive optical powers of +0.25 D is generated by creating a certain electrical potential profile across the electro-active lens 310, while a negative optical power of −0.25 D is created when the opposite of that electrical potential profile is applied across the electro-active lens 310. This results in changing the index of refraction profile through the lens, producing the diverging power. In either case, the electrical potential across the electro-active lens 310 causes the electro-active material inside the electro-active lens 310 to orient in such a manner that viewing though the lens causes a 0.25 D difference in optical power compared to the lens when no potential is applied across the lens. It should be appreciated that each electro-active lens has no optical power when the elect-o active lens is not activated, such as when there is no potential applied across the lens.

A second electro-active lens 320 in this embodiment has an optical power of 0.75 D when the electro-active lens 320 is activated, while a third electro-active lens 330 has an optical power of 2.25 D when the electro-active lens 330 is activated. Whether the optical power in each electro-active lens is either a positive or negative optical power depends upon the distribution of the electrical potential applied across each lens, which, as discussed earlier is independent of the distribution of electrical potential applied to the other lenses. The fourth lens 340 has an optical power of 6.75 D. It should be appreciated that although the lenses 310, 320, 330, 340 are shown in FIG. 3 as arranged in increasing optical power, the optical power, of the lenses is always additive regardless of the order and they may be arranged in any manner.

In certain embodiments of the invention, it may be desirable to use an electro-active lens as the fourth lens 340 that has an optical power of 6.75 D when the electro-active lens is activated. In other circumstances, it may be desirable to use a conventional lens as the fourth lens 340. In these embodiments, a positive or negative conventional lens having an optical power of 6.75 can be rotated into or out of the series of electro-active lenses to produce the desired net optical power.

As shown in Table 1, every optical power between −10.0 D to +10.0 D is available in 0.25 D increments and the electrical potential profile applied across each electro-active lens can be varied as necessary to achieve appropriate vision correction for a particular patient. Although Table 1 only shows optical powers between 0 and +10.0 D, appropriate negative powers could be obtained by simply reversing the sign of each optical power on the chart to determine the direction of the electrical potential for each lens. For example, if a net optical power of +0.50 D is desired, the electrical potential across the 0.25 D electro-active lens is directed to create an optical power of −0.25 D while the electrical potential across the 0.75 D electro-active lens is directed to impart an optical power of +0.75 D to the electro-active lens. When a patient looks through the series of lenses, the net optical power is the sum of all of the optical powers of the lenses in the series and produces the desired +0.50 D. Viewing through tenses in the series that do not have an electrical potential across them creates no change in the optical power and does not affect the net optical power as it appears to the patient. If a net optical power of −0.50 D is desired, the direction of the potential across the 0.25 D and the 0.75 D lenses is switched so that the optical powers produced by each powered lens is +0.25 D and −0.75 D respectively, for a net optical power of −0.50 D.

TABLE 1

| Optical Power (in D) | Lens | | | |
|---|---|---|---|---|
| | 0.25 D | 0.75 D | 2.25 D | 6.75 D |
| +0.00 | 0 | 0 | 0 | 0 |
| +0.25 | + | 0 | 0 | 0 |
| +0.50 | − | + | 0 | 0 |
| +0.75 | 0 | + | 0 | 0 |
| +1.00 | + | + | 0 | 0 |
| +1.25 | − | − | + | 0 |
| +1.50 | 0 | − | + | 0 |
| +1.75 | + | − | + | 0 |
| +2.00 | − | 0 | + | 0 |
| +2.25 | 0 | 0 | + | 0 |
| +2.50 | + | 0 | + | 0 |
| +2.75 | − | + | + | 0 |
| +3.00 | 0 | + | + | 0 |
| +3.25 | + | + | + | 0 |
| +3.50 | − | − | − | + |
| +3.75 | 0 | − | − | + |
| +4.00 | + | − | − | + |
| +4.25 | − | 0 | − | + |
| +4.50 | 0 | 0 | − | + |
| +4.75 | + | 0 | − | + |
| +5.00 | − | + | − | + |
| +5.25 | 0 | + | − | + |
| +5.50 | + | + | − | + |
| +5.75 | − | − | 0 | + |
| +6.00 | 0 | − | 0 | + |
| +6.25 | + | − | 0 | + |
| +6.50 | − | 0 | 0 | + |
| +6.75 | 0 | 0 | 0 | + |
| +7.00 | + | 0 | 0 | + |
| +7.25 | − | + | 0 | + |
| +7.50 | 0 | + | 0 | + |
| +7.75 | + | + | 0 | + |
| +8.00 | − | − | + | + |
| +8.25 | 0 | − | + | + |
| +8.50 | + | − | + | + |
| +8.75 | − | 0 | + | + |
| +9.00 | 0 | 0 | + | + |
| +9.25 | + | 0 | + | + |
| +9.50 | − | + | + | + |
| +9.75 | 0 | + | + | + |
| +10.00 | + | + | + | + |

To further improve the accuracy with which an individual's vision prescription may be determined, an additional lens, preferably an electro-active lens, with an optical power of 0.125 D may be added. It should be appreciated that a lens having an optical power of 0.125 D may sometimes be referred to as a 0.12 D lens by those ordinarily skilled in the art, although the optical power is actually 0.125 D The addition of a 0.125 D lens permits vision correction to be measured, and thus a vision prescription to be determined, between −10.0 D and +10.0 D in 0.125 D increments. This gives an eye-care professional increased flexibility in fine tuning the patient's vision correction to provide the patient with a more accurate vision prescription. If desired, additional, weaker lenses could be added to the series of lenses of the phoropter; each of which provides half of the optical power of the previous lens added, furthering decreasing the increments in which changes in optical power are presented to the patient to determine the vision prescription, such as adding a 0.0625 D lens for example.

It should also be appreciated that the 0.125 D lens may be an electro-active lens that may be included within the series of lenses in the phoropter. Alternatively, if the 0.125 lens is a conventional lens, it may be used as an external flip lens that can be either automatically or manually flipped or rotated into place in front of the series of lenses contained within the phoropter by the eye-care professional at an appropriate time during the eye examination.

The electro-active phoropter also comprises a power supply individually connected to each of the electro-active lenses that is capable of creating the electrical potential across the electro-active lens to result in a positive or negative optical power. Referring again to FIG. 2, typically, the electro-active lenses are controlled by a single control unit 250 coupled to the electro-active lenses of the phoropter 200, such as through the bundled conductors 255, fob example. The control unit 250 is positioned such that the eye care professional can easily adjust the power supplied to each electro-active lens to progressively change the net optical power of the phoropter. As a patient looks through the series of lenses 220, 230 of the phoropter 200 at an eye chart, the patient may give verbal feedback based on the clarity of images the patient sees for particular optical powers. The net optical power of each series of lenses 220, 230 can be changed in any number of ways, such as a dial 265, 266 to increase or decrease the optical power for each eye. The switching of each electro-active lens may be programmed into the control unit 250 by configuring the control unit 250 to internally adjust the electrical potential applied across each electro-active lens as shown in Table 1 based upon a desired optical power. In this way, the eye-care professional does not need to remember, which electro-active lens has a positive or negative power; and needs only to use the dials 265, 266 to increase or decrease the optical power for each eye. In embodiments in which one or more conventional lenses 260, 262 are used, the eye-cue professional may still need to mechanically rotate the conventional lenses 260, 262 into or out of the series of lenses 220, 230 to produce the desired net optical power It should be appreciated that with respect to the correction of conventional refractive error, such as spherical error, the patient could be given direct control over activating or deactivating the series of lenses 220, 230 of the phoropter 200 to achieve a desired vision correction. For example, the control unit 250 that sends electrical power to each electro-active lens to create an electrical potential to be applied across a particular lens in the phoropter may permit the user to simply, by way of example only, press a button or turn a dial to increase of decrease the optical power for each eye.

Figure 4:
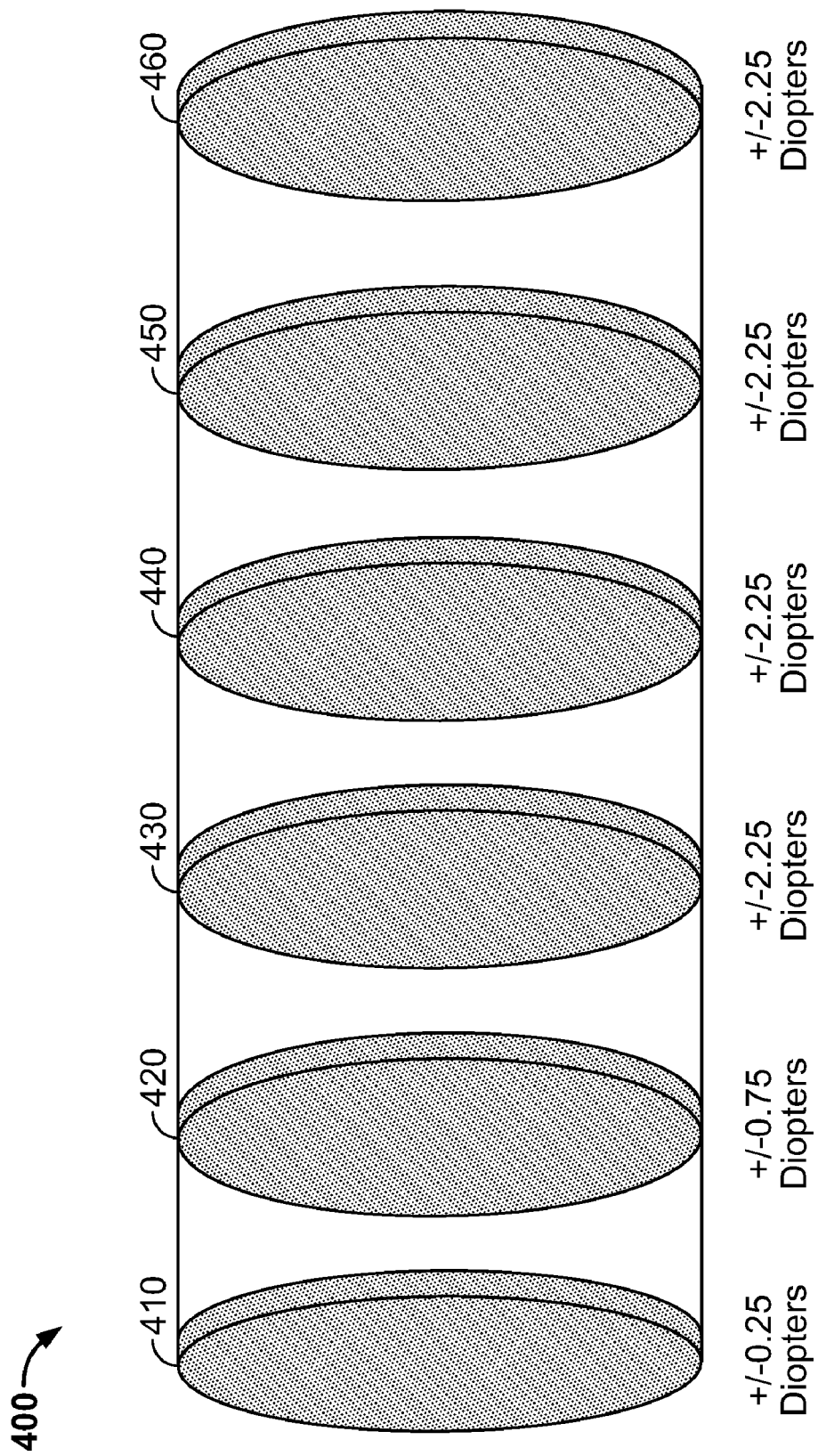
FIG. 4 illustrates a series of lenses of an electro-active phoropter in accordance with another exemplary embodiment of the invention.

In another exemplary embodiment of the invention, the electro-active phoropter uses a series of six electro-active lenses to provide vision correction and determine a vision prescription between −10.0 D and +10.0 D in 0.25 D steps. As shown in FIG. 4, a series 400 of six electro-active lenses 410, 420, 430, 440, 450, 460 are used in the phoropter. As in the previous embodiment discussed with respect to FIG. 3, three of the electro-active lenses 410, 420, 430 again have an optical power of 0.25 D, 0.75 D, and 2.25 D, respectively. However, as shown in FIG. 4, the 6.75 D lens is replaced with three additional electro-active lenses 440, 450, 460 each having an optical power of 2.25 D. The net optical power produced by the phoropter is shown in Table 2 along with the setting of whether each lens is producing positive, negative or no optical power to produce the desired net optical power.

TABLE 2

| Optical Power (in D) | Lens | | | | | |
|---|---|---|---|---|---|---|
| | 0.25 D | 0.75 D | 2.25 D | 2.25 D | 2.25 D | 2.25 D |
| +0.00 | 0 | 0 | 0 | 0 | 0 | 0 |
| +0.25 | + | 0 | 0 | 0 | 0 | 0 |

TABLE 2-continued

| Optical Power (in D) | Lens | | | | | |
|---|---|---|---|---|---|---|
| | 0.25 D | 0.75 D | 2.25 D | 2.25 D | 2.25 D | 2.25 D |
| +0.50 | − | + | 0 | 0 | 0 | 0 |
| +0.75 | 0 | + | 0 | 0 | 0 | 0 |
| +1.00 | + | + | 0 | 0 | 0 | 0 |
| +1.25 | − | − | + | 0 | 0 | 0 |
| +1.50 | 0 | − | + | 0 | 0 | 0 |
| +1.75 | + | − | + | 0 | 0 | 0 |
| +2.00 | − | 0 | + | 0 | 0 | 0 |
| +2.25 | 0 | 0 | + | 0 | 0 | 0 |
| +2.50 | + | 0 | + | 0 | 0 | 0 |
| +2.75 | − | + | + | 0 | 0 | 0 |
| +3.00 | 0 | + | + | 0 | 0 | 0 |
| +3.25 | + | + | + | 0 | 0 | 0 |
| +3.50 | − | − | + | + | 0 | 0 |
| +3.75 | 0 | − | + | + | 0 | 0 |
| +4.00 | + | − | + | + | 0 | 0 |
| +4.25 | − | 0 | + | + | 0 | 0 |
| +4.50 | 0 | 0 | + | + | 0 | 0 |
| +4.75 | + | 0 | + | + | 0 | 0 |
| +5.00 | − | + | + | + | 0 | 0 |
| +5.25 | 0 | + | + | + | 0 | 0 |
| +5.50 | + | + | + | + | 0 | 0 |
| +5.75 | − | − | + | + | + | 0 |
| +6.00 | 0 | − | + | + | + | 0 |
| +6.25 | + | − | + | + | + | 0 |
| +6.50 | − | 0 | + | + | + | 0 |
| +6.75 | 0 | 0 | + | + | + | 0 |
| +7.00 | + | 0 | + | + | + | 0 |
| +7.25 | − | + | + | + | + | 0 |
| +7.50 | 0 | + | + | + | + | 0 |
| +7.75 | + | + | + | + | + | 0 |
| +8.00 | − | − | + | + | + | + |
| +8.25 | 0 | − | + | + | + | + |
| +8.50 | + | − | + | + | + | + |
| +8.75 | − | 0 | + | + | + | + |
| +9.00 | 0 | 0 | + | + | + | + |
| +9.25 | + | 0 | + | + | + | + |
| +9.50 | − | + | + | + | + | + |
| +9.75 | 0 | + | + | + | + | + |
| +10.00 | + | + | + | + | + | + |

As before, additional lenses weaker than 0.25 D may be used in the series of lenses to improve the accuracy of the vision prescription by decreasing the increments of vision correction.

Figure 5:
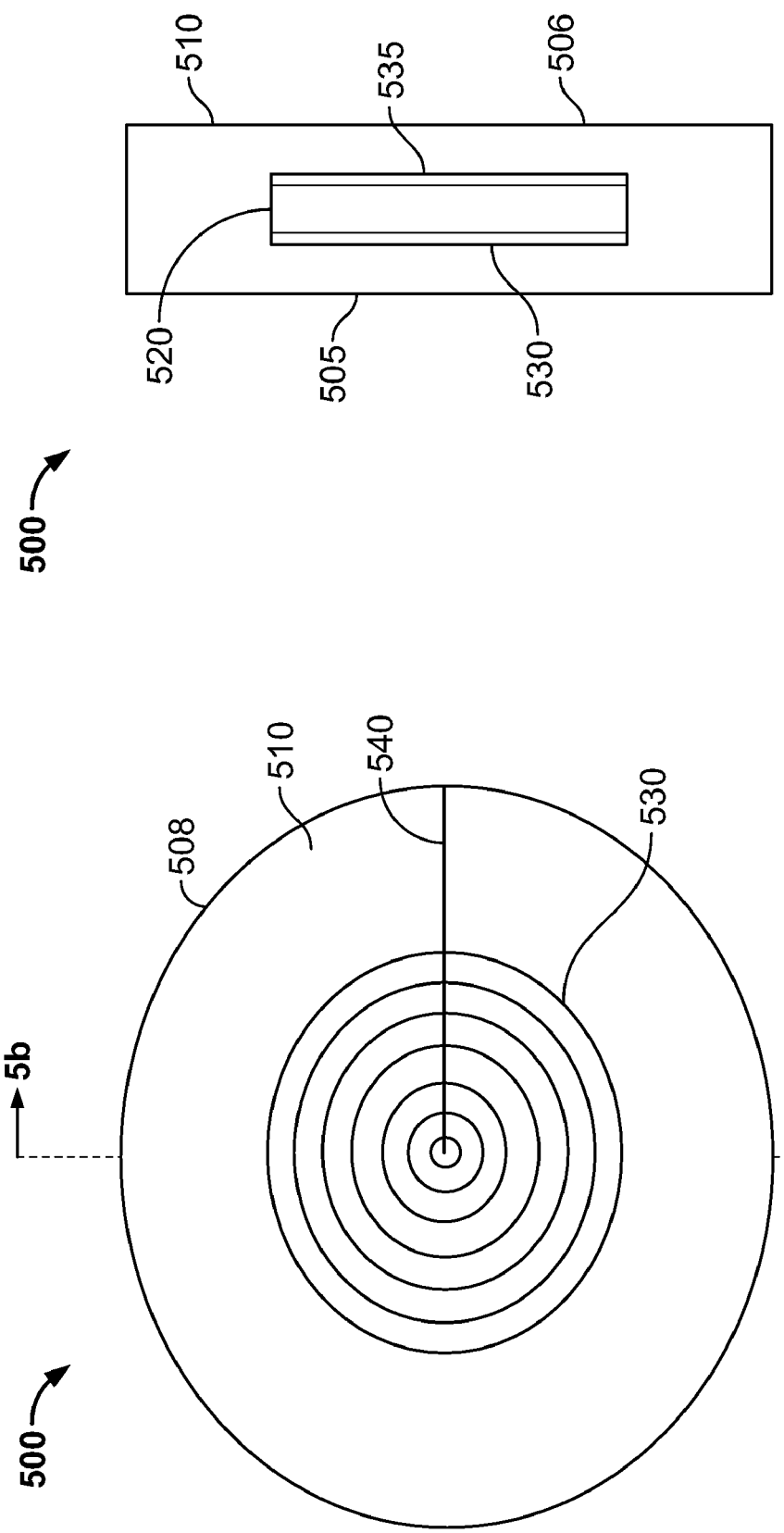
FIGS. 5a and 5b illustrate a fixed pattern pixelated electro-active lens for use in exemplary embodiments of the invention.

The electro-active lenses described with respect to the preceding embodiments may be any type of electro-active lens, but are typically fixed pattern pixelated electro-active lenses, as shown in FIGS. 5a and 5b. A fixed pattern pixelated electro-active lens comprises a lens substrate 510 that contains an electro-active material 520 disposed between transparent electrodes 530, 535. The lens substrate 510 may be manufactured from any rigid, optically transparent material suitable for manufacturing eyeglasses, such as glass or acrylics, for example. Electro-active materials 520 include suitable for use in the electro-active lens 400 liquid crystals, such as nematic or smectic liquid crystals, cholesteric liquid crystals, electro-optic polymers, polymer liquid crystals, for example, or any other optically transparent material that undergoes a change in index of refraction in response to applied electrical potential. The electrodes 530, 535 are optically transparent, conductive electrodes manufactured from materials such as tin oxide, indium oxide, or indium tin oxide, or transparent conductive polymers, for example.

For the correction of conventional refractive error, such as spherical correction, the electrodes 530, 535 are typically concentric rings. The rings of electrodes advance outward from the center of the lens 500 to the outer portion of the lens that contains the electro-active material to produce a plurality of circular pixels. Although the lens 500 may contain electro-active material 520 to only cover a portion of the front and back surfaces 505, 506 of the lens 500, the lens 500 may also contain electro-active material 520 that extends outward to the edge 508 of the lens itself. The fixed pattern pixelated electro active lens 500 has the same optical power over the entire area of the lens that contains the electro-active material 520, and that optical power is one of a positive, negative or neutral optical power.

Figure 10A:
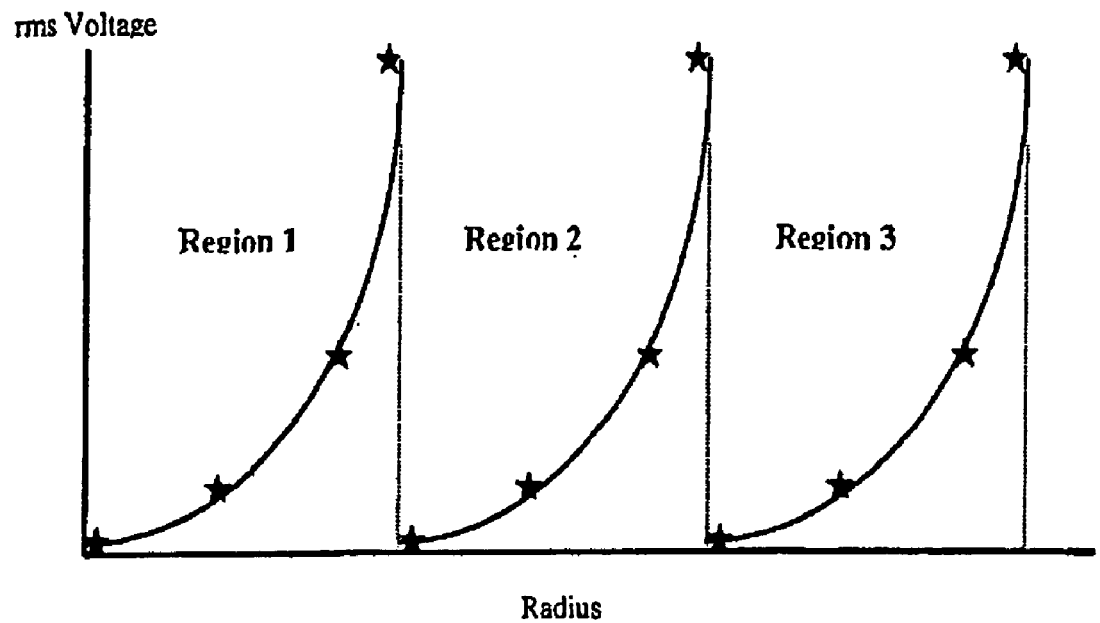
FIG. 10a illustrates the spatial voltage profile for a diverging pixelated electro-active lens
Figure 10B:
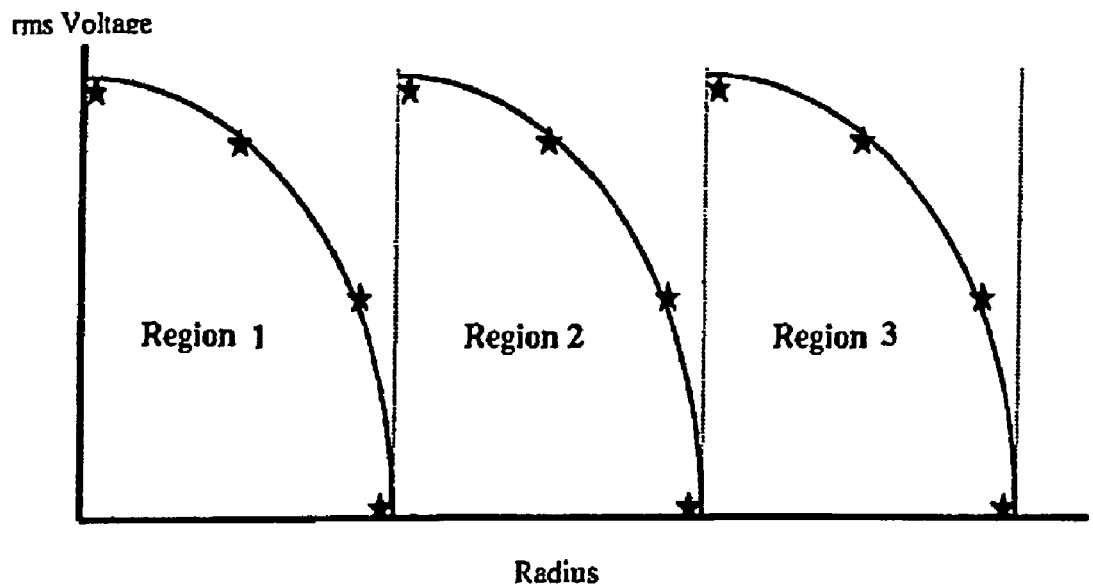
FIG. 10b illustrates the spatial voltage profile for a converging pixelated electro-active lens.

Each of the concentric rings of electrodes may be connected by a conductor 540 that extends out from the lens 500 and connects to a power source, such as the control unit that can use battery power or be plugged into a standard outlet. When a current is passed through the electrodes 530, 535 an electric potential is created across the lens that causes the electro-active material to orient in a direction that produces a change in refractive index and accordingly the desired optical power. Depending upon the electrical potential placed on each electrode across the lens, a different index of refraction profile is produced across the lens that directly affects the sign and magnitude of the optical power produced FIGS. 10a and 10b show in more detail how the electrical potential distribution across a fixed pattern pixelated electro-active lens is modified to provide positive or negative optical power for an electro-active material in which the effective index of refraction of the electro-active material is increased with increasing voltage. By effective index of refraction is meant the index that light experiences as it passes through the lens. In each case, the distribution produces a repeating profile for each ring of electrodes when the root mean square (rms) voltage is plotted versus the radial distance from the center of the lens. With respect the diverging electro-active lens profile of FIG. 10a that produces a negative optical power when the electro-active material is activated, an electric voltage is applied to each ring to produce an rms voltage profile that has an rms voltage that is lowest near the center of the lens and that increases as the distance for the center of the lens. Likewise, FIG. 10b shows a converging lens profile in which the applied electrical potential is greatest in each ring at the nearest distance of the ring to the center of the lens and decreases as the radial distance increases. The rms voltage profile may be switched to go from a diverging to a converging lens by switching the voltages applied at various points within each ring of electrodes. For example, if the diverging lens uses four voltages for each ring having an increasing voltage of 1V, 2V, 3V, and 4V, a converging lens to produce the same optical power would have voltages applied at the same four points, but in the reverse order: 4V, 3V, 2V and 1V. This has the effect of flipping the rms voltage profile and modifying the index of refraction of the electro-active material to obtain the desired results. It should be appreciated that FIGS. 10a and 10b are exemplary and that many electrodes may be used to produce a uniform rms voltage profile and achieve good optical efficiency.

Figure 6:
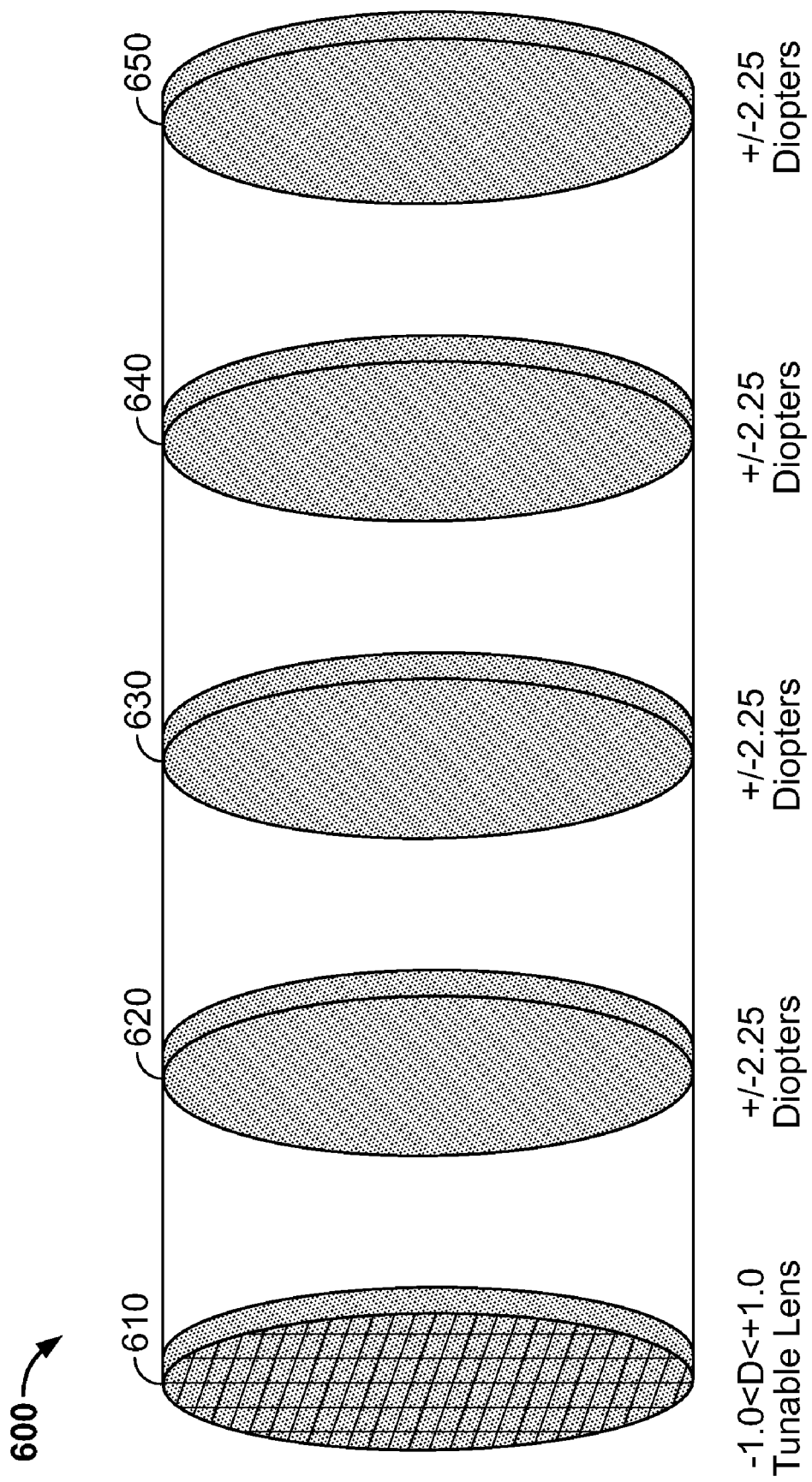
FIG. 6 illustrates a series of lenses of an electro-active phoropter in accordance with an exemplary embodiment of the invention including a finely-pixelated and fixed pattern pixelated electro-active lenses

Other embodiments of the invention may advantageously include other pixelated electro-active lenses, such as a finely-pixelated electro-active lens. FIG. 6 illustrates an exemplary embodiment of a series of electro-active lenses 600 in which a single, finely pixelated electro-active lens 610 replaces the fixed pattern pixelated electro-active lenses of 0.25 D and 0.75 D optical power. The finely pixelated electro-active lens 610 is tunable and can be adjusted to any optical power, by way of example only, between −1.0 D to +100 D. This provides an electro-active phoropter that can provide vision correction between −10.0 D to +10.0 D in any Diopter increment.

For electro-active lenses that are finely pixelated, the electro-active lens comprises a grid array of electro-active material using a transparent insulating material to create individual pixels of electro-active material. Each pixel is separated from adjacent pixels by the insulating material and is individually connected to an electrode. In this manner, each pixel is individually addressable to vary the index of refraction of the electro-active material within that particular grid section of the array. By adjusting the optical power of each fine pixel individually, the phoropter may also be used to correct non-conventional refractive error also known as higher order aberrations such as, by way of example only, coma, irregular astigmatism, spherical aberration, trefoil, tetrafoil, pentafoil, hexafoil, and the like. Various embodiments of these and other electro-active lenses are explained in more detail in U.S. Pat. No. 6,619,799 to which this application claims priority and which has been earlier incorporated by reference in its entirety.

Figure 7:
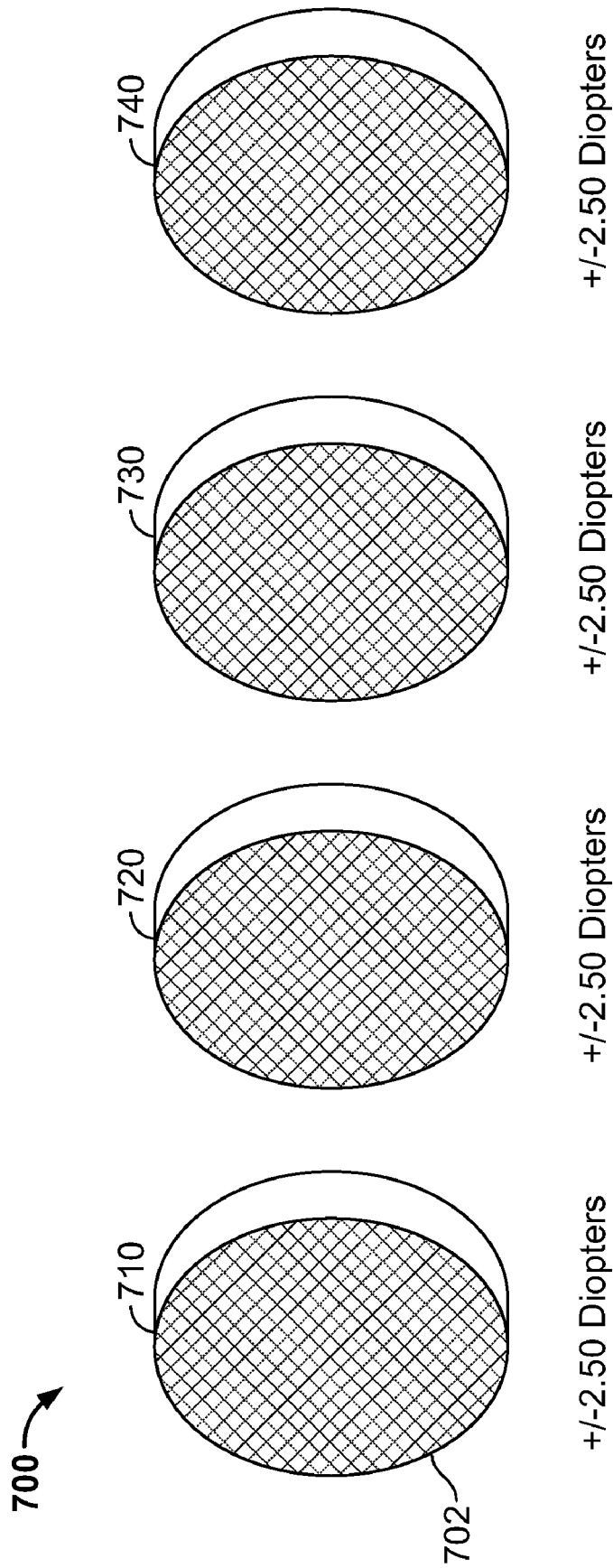
FIG. 7 is a series of finely-pixelated lenses of a phoropter in accordance with an exemplary embodiment of the invention.

In another exemplary embodiment of the invention, the phoropter comprises four electro-active lenses, each of which has a maximum optical power of 2.50 D. In this embodiment, as shown in more detail in FIG. 7, each electro-active lens 710, 720, 730, 740 in the series 700 of electro-active lenses is finely pixelated. In this embodiment, not only is each electro-active lens individually addressable, but each electro-active lens in the series 700 further comprises an array of fine pixels 702, in which each fine pixel is itself individually addressable. Thus, each pixel can independently provide a positive, negative, or no optical power. Further, the use of finely pixelated lenses also permits the electrical potential across each pixel of the electro-active lens to be adjusted to produce any optical power that is between the maximum and minimum optical power of the lens, unlike the fixed pattern pixelated electro-active lens which has an optical power of a single magnitude when the fixed pattern pixelated electro-active lens is activated.

Each finely pixelated electro-active lens can produce continuous optical power from −2.50 D to +2.50 D, so that the lens series 700 is capable of producing a net optical power of between −10.0 D and +10.0 D that can be incremented in any desired step of increasing or decreasing optical power. Rather than adjusting the potential across multiple lenses at the same time to achieve the desired optical power, the eye-care professional can adjust a single lens in incremental optical steps, such as 0.25 D for example. When one electro-active lens cannot provide optical power of any greater magnitude, that electro-active lens is left at its maximum optical power and another electro-active lens in the series may be activated to increase the magnitude of the net optical power until the patient can see the eye chart clearly and the vision prescription has been determined.

For example, referring again to FIG. 7, when a patient requiring positive vision correction looks through a phoropter with multiple finely pixelated electro-active lenses, a first lens 710 may be activated in +0.25 D steps until the lens has reached a maximum optical power of +2.50 D. If the patient still does not have clear vision, the eye-care professional keeps the first lens 710 at +2.50 D and activates the next electro-active lens 720 in the series 700 to produce a net optical power until the patient can see clearly. The eye-care professional may activate the third and fourth electro-active lenses 730, 740 in the series 700 as necessary to produce the appropriate optical power.

Vision prescriptions for bifocal and other multi-focal lenses may be obtained in a similar manner using various embodiments of the invention by simply varying the distance between the patient and the eye chart or other object used to determine visual clarity. The optical power that provides the patient vision correction at different focal points may be measured to obtain a complete vision prescription for the patient that can be used to create multi-focal spectacles, contact lenses, and ocular lenses with the appropriate combination of optical power.

In addition to measuring conventional refractive error using the series of electro-active lenses as described, exemplary embodiments of the phoropter may also be used to measure and correct astigmatic error. In these embodiments, the phoropter comprises at least one lens with cylinder power to correct for astigmatic error. The lens may be a conventional lens that can be rotated into or out of the series of lenses of the phoropter used to correct spherical error, followed by rotating that lens while it is front of the eye to adjust cylinder axis. Alternatively, the lens may be an electro-active lens, such as a fixed pattern pixelated electro-active lens or a finely pixelated electro-active lens designed and energized to measure and correct astigmatism.

Figure 8:
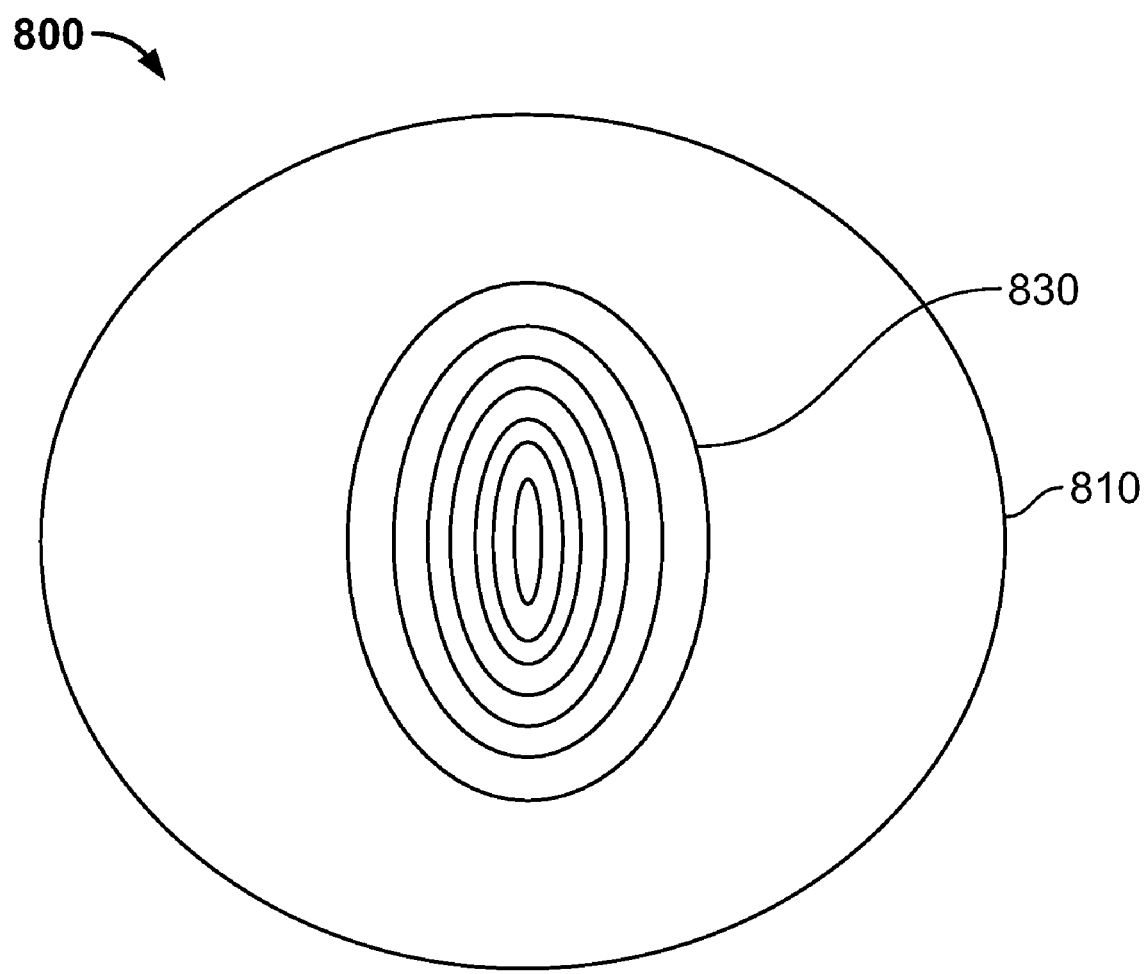
FIG. 8 is a fixed pattern pixelated electro-active lens for the correction of astigmatic error in accordance with an exemplary embodiment of the invention.

In exemplary embodiments of the invention that include an electro-active lens to correct astigmatic errors, a fixed pattern pixelated electro-active lens, such as the electro-active lens 800 shown in FIG. 8 may be used. The electro-active lens 800 comprises elliptically symmetric electrodes 810 that, when activated, create an elliptical area of increased optical power that may be used by the eye-care professional to determine cylinder correction. When no electrical potential is applied across the lens 800, it produces no optical power and the lens does not need to be removed from the series of lenses when astigmatic error is not being measured. When the fixed pattern pixelated electro-active lens 800 is activated and used to correct and measure astigmatic error, the lens 800 still needs to be rotated while in front of the eye. This rotation results in adjusting the axis correction orientation of the ellipse to determine proper cylinder correction. Rotation of the lens 800 may be achieved by conventional mechanical or, electro-mechanical methods.

Figure 9B:
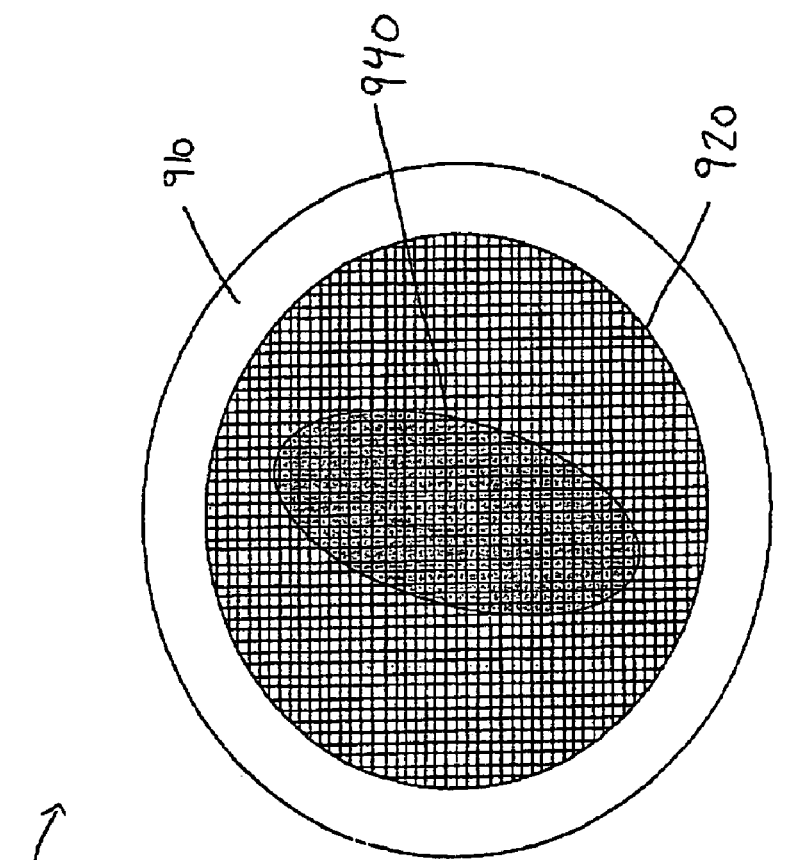
FIGS. 9a and 9b illustrate a finely-pixelated electro-active lens for the correction of astigmatic error in accordance with an exemplary embodiment of the invention.
Figure 9A:
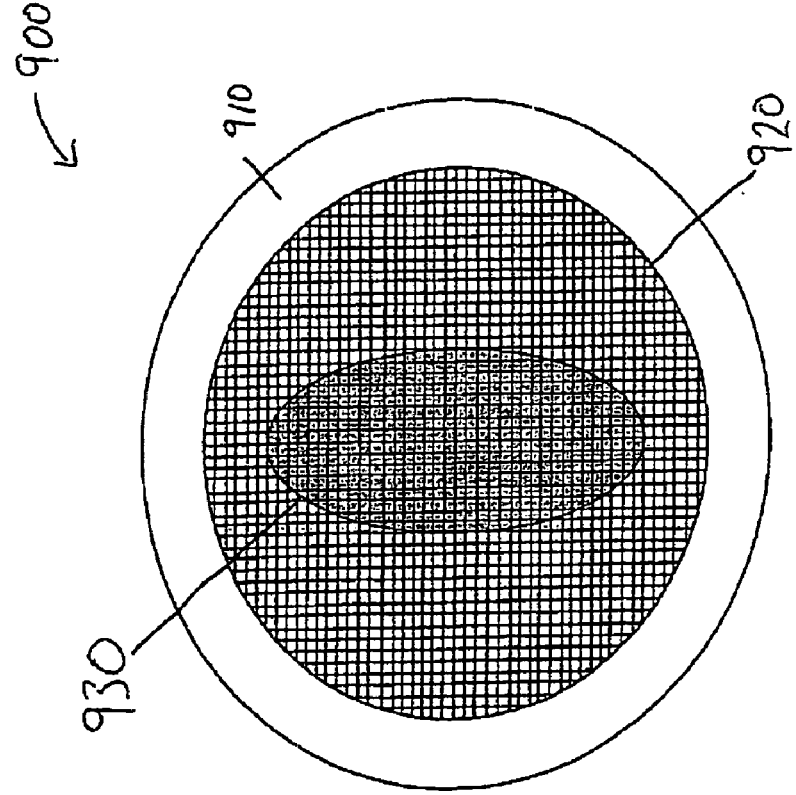

Conversely, by using a finely pixelated electro-active lens to measure conventional astigmatic error; no rotation of the lens is necessary. Instead, the elliptical or toric power could be axis-rotated by activating or deactivating appropriate pixels of the finely-pixelated electro-active lens to create an elliptical or toric optical power. This achieves the same function as actually rotating other lenses FIGS. 9a and 9b illustrate an electro-active lens 900 that includes a lens substrate portion 910. The electro-active lens is mostly pixelated, having a finely pixelated area 920 that extends from the center outward, covering more than 50% of the lens area.

As shown in FIG. 9a, certain pixels of the electro-active lens 900 may initially be activated to produce an elliptical pattern 910 that has a vertical major axis to provide elliptical or toric power. Instead of mechanical or electro-mechanical rotation of the electro-active lens 900 to adjust the axis correction orientation of the ellipse, the elliptical pattern is rotated by activating a different set of pixels that correspond to a second elliptical pattern 920 as shown FIG. 9b, in which the ellipse's major axis is tilted a certain number of degrees. The elliptical pattern may continue to be rotated in this manner of activating and deactivating pixels until the patient's astigmatic power error and axis is determined.

In a similar manner, prismatic refraction can also be accomplished by including conventional prismatic lenses in the electro-active phoropter for the measurement of prismatic error. Alternatively, a fixed pattern pixelated electro-active lens may be used having a prismatic electrode pattern. Fixed pattern pixelated electro-active lenses would require mechanical rotation as described with respect to astigmatic correction. Also like the astigmatic correction, a finely-pixelated electro-active lens may be employed in which the prismatic pattern can be created at any orientation with respect to the electro-active lens by activating and deactivating pixels. The various prismatic patterns produced by the finely pixelated lens can be presented to the patient at various angles to provide vision correction and determine an appropriate prismatic power and prism orientation Determination of a patient's vision prescription may also include the measurement of higher order aberrations, such as by using a wave front analyzer in combination with various embodiments of the electro-active phoropter. Any technique for wave front analysis may be used. A wave front analysis creates a wave refractive error map of a patient's eye. In some cases, a person may have an aberration on one area of the eye that results in a different vision correction need for that portion of the eye than for other portions of the eye such as by way of example only, coma. By determining the complete vision prescription of the entire eye, including measuring and correcting for the patient's higher older aberrations, a patient's vision may be corrected to better than 20/20, such as 20/15 or 20/10 for example, and may even approach 20/8, the theoretical limit of vision correction Once the wave front analysis has been generated for a patient's eye, individual pixels of the electro-active lens series of the phoropter may be adjusted to correct the patient's vision prescription for the particular area of the eye that views through that pixel. The patient can view through the phoropter in a mostly simultaneous manner at an eye chart to assist, measure, and confirm whether the portion of the vision prescription determined with the wave front analyzer provides the enhanced vision correction desired and confirm that the overall vision prescription determined for the patient corrects both conventional and non-conventional refractive errors. By "mostly simultaneous manner" is meant that while the wave front analyzer is providing data and measurements to the electro-active phoropter, the phoropter is adjusting the electro-active lenses to allow the patient to see in nearly teal time the correction being suggested by the wave front analyzer. This allows for either one or both of an objective examination of the patient and a subjective examination of the patient using input from the patient based on the clarity.

Once the final vision prescription is determined, it may be recorded so that the patient can have the prescription filled. The prescription may be visually displayed to a screen on or connected to the control unit and manually recorded by the eye care professional. In other exemplary embodiments of the invention, the prescription may be electronically recorded, such as by saving it to a memory storage device like a disk, for example. The vision prescription may also be sent electronically, such as by electronic mail, from the eye-care professional to the patient and/or to an optician or laboratory for lens fabrication. Alternatively, of in combination with other methods of recording the prescription, the phoropter may record the vision prescription by producing a print-out of the vision prescription, such as a script that is ready for signature by the eye-care professional and that the patient may take to an optician to be filled.

If the vision prescription is saved to disk or other memory storage device, and the patient desires electro-active eyeglasses, ocular or contact lenses, the saved vision prescription may be used to directly program the patient's new prescription. In certain circumstances, such as when an electro-active pair of eyeglasses is being utilized as shown in FIG. 1, the vision prescription can be recorded directly to a memory device, such as a computer chip, on the frame and/or lens portion of the electro-active eye glasses. The frame and/or lens portion may then be connected to a mobile power supply such as battery and disconnected from the control unit and the patient can walk away with a new prescription already programmed into new electro-active spectacles. Likewise, the patient could later return and his electro-active eyeglasses can be reconnected to the control unit to determine and record a new vision prescription directly to the spectacles. Thus, the patient can have an electro-active eye examination and can leave the examination with electro-active eyeglasses programmed to a proper prescription immediately after the examination is completed.

The present invention is not to be limited in scope by the specific embodiments described herein. Indeed, various modifications of the present invention, in addition to those described herein, will be apparent to those of ordinary skill in the art from the foregoing description and accompanying drawings. Thus, such modifications are intended to fall within the scope of the following appended claims. Further, although the present invention has been described herein in the context of a particular implementation in a particular environment for a particular purpose, those of ordinary skill in the art will recognize that its usefulness is not limited thereto and that the present invention can be beneficially implemented in any number of environments for any number of purposes. Accordingly, the claims set forth below should be construed in view of the full breadth and spirit of the present invention as disclosed herein.

What is claimed is:

1. A phoropter for measuring a refractive error of an eye, comprising:
    a lens having an optical power, wherein said lens is adapted for altering said optical power from a first optical power to a second optical power while housed in the phoropter.
2. The phoropter of claim 1, wherein the phoropter can be worn by a wearer.
3. The phoropter of claim 2, wherein the phoropter is adapted for use as an eyewear for said wearer.
4. The phoropter of claim 1, wherein the phoropter is a refractor.
5. The phoropter of claim 1, wherein the phoropter comprises an auto-refractor.
6. The phoropter of claim 1, wherein the phoropter is operably connected to an auto-refractor.
7. The phoropter of claim 1, wherein said lens is an electro-active lens.
8. The phoropter of claim 1, wherein said lens is programmable.
9. The phoropter of claim 1, wherein the phoropter is adapted for providing a measurement of a wearer's refractive error.
10. The phoropter of claim 1, wherein the phoropter is operably connected to a controller.
11. The phoropter of claim 1, wherein the refractive error is one of myopia, hyperopia, presbyopia, regular astigmatism, or a refractive error other than myopia, hyperopia, presbyopia, and regular astigmatism.

* * * * *